(12) United States Patent
Fester et al.

(10) Patent No.: US 7,655,206 B2
(45) Date of Patent: Feb. 2, 2010

(54) PROCESS FOR THE MANUFACTURE OF HYDROGEN-RICH CYCLOSILOXANE

(75) Inventors: Gerrit Fester, Auerbach / V. (DE); Gerhard Roewer, Freiberg (DE); Edwin Kroke, Freiberg (DE)

(73) Assignee: Evonik Degussa GmbH, Essen (DE)

( * ) Notice: Subject to any disclaimer, the term of this patent is extended or adjusted under 35 U.S.C. 154(b) by 19 days.

(21) Appl. No.: 12/278,522

(22) PCT Filed: Apr. 19, 2007

(86) PCT No.: PCT/DE2007/000723

§ 371 (c)(1), (2), (4) Date: Aug. 6, 2008

(87) PCT Pub. No.: WO2007/118473

PCT Pub. Date: Oct. 25, 2007

(65) Prior Publication Data

US 2009/0041649 A1  Feb. 12, 2009

(30) Foreign Application Priority Data

Apr. 19, 2006  (DE) .................. 10 2006 019 015

(51) Int. Cl.
*C07F 7/08* (2006.01)
(52) U.S. Cl. ....................... 423/325; 423/324
(58) Field of Classification Search ................ 423/324, 423/325
See application file for complete search history.

(56) References Cited

U.S. PATENT DOCUMENTS

| 2,810,628 | A | * | 10/1957 | Bailey et al. ................ 423/325 |
| 3,989,733 | A | * | 11/1976 | Okamoto et al. ............ 556/460 |
| 2004/0137758 | A1 | | 7/2004 | Li et al. |
| 2007/0173671 | A1 | | 7/2007 | Bohmhammel et al. |

FOREIGN PATENT DOCUMENTS

WO  WO 2007/118474  10/2007
WO  WO 2008/009680  1/2008

OTHER PUBLICATIONS

Seyferth et al, Cyclic Polysiloxanes from the Hydrolysis of Dichlorosilane, 1983, 22, 2163-2167.*
Seyferth et al ("Cyclic Polysiloxanes from the Hydrolysis of Dichlorosilane", Journal of Inorganic Chemistry, 22, 1983, p. 2163-2167).*
Seyferth, Dietmar et al., "Cyclic Polysiloxanes from the Hydrolysis of Dichlorosilane", Inorg. Chem., vol. 22, No. 15, pp. 2163-2167, XP 002444114, (1983).
U.S. Appl. No. 10/584,446, filed Jun. 22, 2006, Bohmhammel, et al.

* cited by examiner

*Primary Examiner*—Roy King
*Assistant Examiner*—Xiaobei Wang
(74) *Attorney, Agent, or Firm*—Oblon, Spivak, McClelland, Maier & Neustadt, L.L.P.

(57) ABSTRACT

The present invention relates to a for controlled synthesis of hydrogen-rich cyclosiloxanes of the $(H_2SiO)_n$ type.

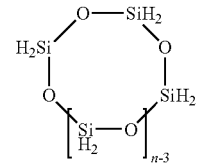

where n is an integer equal to or greater than 3, by reacting:
  a.) a halosilane of the $H_2SiX_2$ type where X=halogen with
  b.) a lithium salt, copper(II) salt or a salt of a metal from main group 2 or transition group 2 of the periodic table of the elements, or a mixture of these salts.

The ring size is advantageously adjustable to n=3, 4, 5, 6 (especially n=4 to 6), such that larger rings are not formed.

In a particularly advantageous embodiment of the process, for the selective preparation of cyclohexasiloxane $(H_2SiO)_6$, after the reaction, the solvent is at least partly removed and then solvent is added again.

10 Claims, No Drawings

PROCESS FOR THE MANUFACTURE OF HYDROGEN-RICH CYCLOSILOXANE

The present invention relates to a process for controlled synthesis of hydrogen-rich cyclosiloxanes of the $(H_2SiO)_n$ type. These compounds may find use, for example, as an additive for sealants and hardeners, or as hydrogenating agents.

Hydrogen-rich cyclosiloxanes have to date been studied principally using calculations. By means of ab initio calculations, it has been possible to forecast the crystal structure data and hence the symmetry of the compounds for small cycles—$(H_2SiO)_n$ where n=3, 4, 5 (T. Kudo, F. Hashimoto, M. S. Gordon, Journal of Computational Chemistry 17 (1996) 1163).

The first hydrogen-rich cyclosiloxanes of the $(H_2SiO)_n$ type were mentioned in the studies by Stock et al. from 1919 and were referred to as "prosiloxane" (A. Stock, C. Somieski, Ber. Dtsch. Chem. Ges. 52 (1919) 695).

In the subsequent decades, presumably owing to the high reactivity of the unsubstituted cyclosiloxanes, there were only very few studies in this field. $H_2SiO$ formed in the gas phase from dichlorosilane and water polymerizes only slowly. In liquid phase, dichlorosilane and water form polycondensates.

The silicon-hydrogen bond is unstable with respect to bases, but also with respect to strong acids at pH values below 1 (see U.S. Pat. No. 2,810,628). In the synthesis of cyclosiloxanes, this often leads to a higher degree of crosslinking of the siloxane by T units. In order to prevent this, various techniques can be employed (D. Seyferth, C. Prud'Homme, G. H. Wiseman, Inorg. Chem. 22 (1983) 2163).

According to U.S. Pat. No. 2,810,628, in the case of use of a mixture of an aprotic solvent (e.g. hexane or diethyl ether) and small amounts of water, the result is a complex product mixture which comprises siloxane rings $(H_2SiO)_n$ where n=4-23. In addition, owing to the formation of hydrogen chloride, more highly condensed ring systems and insoluble residues form (equation (1)):

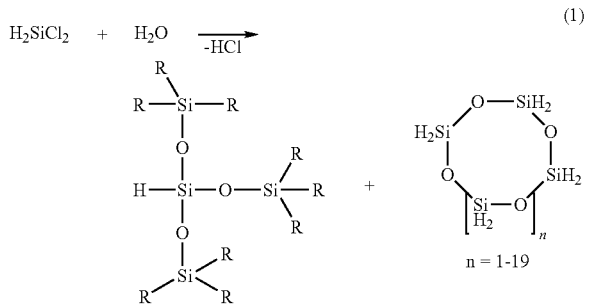

(1)

The cyclic tetramer $(H_2SiO)_4$, the pentamer $(H_2SiO)_5$ and the hexamer $(H_2SiO)_6$ have been detected as main products in the reaction of dichlorosilane with aqueous solvents (D. Seyferth, C. Prud'Homme, Inorg. Chem. 23 (1984) 4412).

Seyferth and coworkers attempted the "controlled" hydrolysis of dichlorosilane with nickel chloride containing water of hydration ($NiCl_2 * 6 H_2O$) in hexane, but without success in relation to the narrowing of the product spectrum (D. Seyferth, C. Prud'Homme, G. H. Wiseman, Inorg. Chem. 22 (1983) 2163).

It is an object of the present invention to specify an improved process for preparing hydrogen-rich cyclosiloxanes.

The object is achieved in accordance with the invention by a process for preparing hydrogen-rich cyclosiloxanes of the type

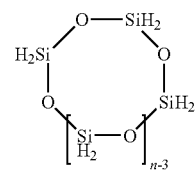

where n is an integer equal to or greater than 3, by reacting:
a.) a halosilane of the $H_2SiX_2$ type where X=halogen with
b.) a lithium salt, copper(II) salt or a salt of a metal from main group 2 or transition group 2 of the periodic table of the elements, or a mixture of these salts.

The process according to the invention is advantageously a one-step process, requires no additions of catalysts and leads selectively to hydrogen-rich (unsubstituted) cyclosiloxanes.

The ring size is advantageously adjustable to n=3, 4, 5, 6 (especially n=from 4 to 6), such that larger rings are not formed. In addition, it is possible to generate defined hydrogen-rich polysiloxane molecules by a gentle ring-opening polymerization.

In order to start the halosilane hydrolysis in practice, even a small concentration of protons is sufficient. In the case of hydrolysis control exclusively with a metal carbonate, this serves as a controlled water donor and as a scavenger of hydrogen chloride with formation of the corresponding metal chlorides, see equation (2), which describes the process with regard to the carbonates of the metals Li (x=2), Ca and Zn (x=1) used with preference:

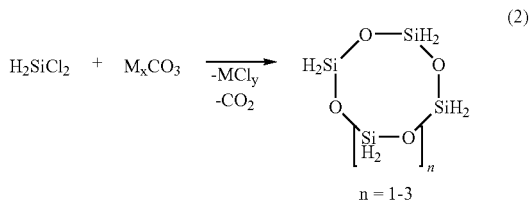

(2)

n = 1-3

M = Ca, Li, Zn
X = 1, 2
$y = \dfrac{2}{x}$

Influencing factors utilized in accordance with the invention for the control of hydrolysis with metal salts are the type of metal ions used, the anions used, the proportion of chemically and physically bound water in the metal salt, and the properties of the organic solvent used, especially the polarity.

The solvents used for the reaction are preferably aprotic solvents, more preferably toluene, n-hexane, n-pentane, petroleum ether, tetrahydrofuran, dioxane, ethyl acetate and glyme, and mixtures of these solvents. In order to avoid side reactions, the solvent is very substantially anhydrous and preferably has a maximum water content of below 0.1%, more preferably below 0.01%. Particularly good results have been achieved with aprotic, nonpolar solvents, especially n-hexane, toluene, n-pentane, cyclohexane, n-heptane. In the more polar aprotic solvents, for example ethyl acetate and THF, larger cycles where n>6 are formed.

Preferred cations of the metal salts are lithium, copper(II) and metal ions of a metal from main group 2 or transition group 2 of the periodic table of the elements, for example $Ca^{2+}$, $Sr^{2+}$, $Ba^{2+}$, $Zn^{2+}$, $Cd^{2+}$; particular preference is given to $Li^+$, $Zn^{2+}$ and $Ca^{2+}$. $Mg^{2+}$ is less preferred.

Preferred anions of the metal salts are hydrogencarbonate and carbonate ions. These decompose under the action of protons to give water and gaseous carbon dioxide. The escape of the carbon dioxide shifts the equilibrium of the reaction advantageously toward the product side.

The process is carried out under virtually anhydrous conditions. The metal salts used, especially carbonates and hydrogencarbonates, are therefore very substantially anhydrous (preferably below 1%, more preferably below 0.1% $H_2O$) and are very substantially free of hydroxide impurities.

The metal salts selected advantageously have limited basicity and hard metal ions which exert a template effect in the hydrolysis/condensation process of the dihalosilane. The salts are also redox-stable with respect to the silicon-hydrogen bond of the siloxane rings.

In apolar solvents, particularly calcium carbonate, lithium carbonate and zinc carbonate are suitable for hydrolysis control. In the case of use of basic, hydrous magnesium hydroxide carbonate (4 $MgCO_3$ * $Mg(OH)_2$ * 5 $H_2O$—frequently referred to as basic magnesium carbonate)—and the more strongly basic sodium carbonate, undesired side reactions occur. The excessively basic action of latter salts causes an undesired nucleophilic attack on the silicon-hydrogen bonds. However, the use of pure, hydroxide-free magnesium carbonate is possible.

The dihalosilanes used are preferably dichlorosilane $H_2SiCl_2$ and $H_2SiF_2$, and also, less preferably, dibromosilane $H_2SiBr_2$. Dichlorosilane is prepared in large amounts for the semiconductor industry and is therefore advantageously an inexpensive starting material.

The dihalosilane is hydrolyzed preferably with from 0.5 to 2, more preferably with from 0.75 to 1.25, molar equivalents (based on the halosilane) of metal salt to give the desired cyclosiloxane. Preferably 20 mmol of $H_2SiCl_2$ are used for from 10 ml to 80 ml of solvent, preferably from 15 ml to 25 ml of solvent.

The cyclic siloxanes $(H_2SiO)_n$ prepared by the process according to the invention are storage-stable in solution.

The formation of small ring sizes proceeds preferentially at low temperatures. A further reason for carrying out the reaction with cooling is the low boiling point of the dichlorosilane (8.9° C.). The synthesis is preferably carried out at a temperature of from −80 to +40° C., preferably from −70 to +10° C., more preferably from −20° C. to +5° C. Particularly in the case of small rings (n=from 3 to 6, especially n=3), the temperature is selected below 10° C., preferably from −70 to 0° C. Since the reaction is exothermic, the reaction mixture is cooled to the appropriate temperature, preferably with an ice bath or an alcohol/dry ice mixture.

The mixture of zinc carbonate as the metal salt and hexane or toluene as the solvent brought the best results, equation (3):

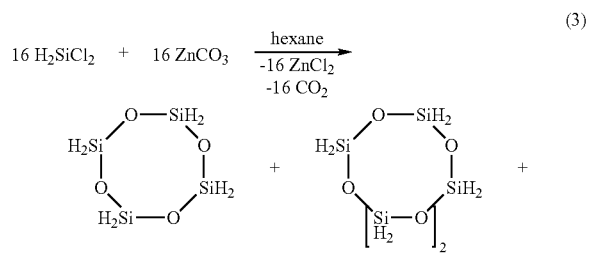

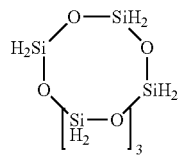

After the reaction described, the inorganic salts are removed, for example by decantation or filtration.

In a particularly advantageous embodiment of the process, to selectively prepare cyclohexasiloxane $(H_2SiO)_6$, after the above-described reaction (after removal of the salts), the solvent is at least partly removed and then solvent is added again.

Surprisingly, simple concentration and subsequent dilution achieves a rearrangement of the smaller cyclosiloxane rings $(H_2SiO)_4$ and $(H_2SiO)_5$ to cyclohexasiloxane $(H_2SiO)_6$ and hence enables a very selective synthesis of cyclohexasiloxane $(H_2SiO)_6$.

The solvent is removed preferably by a distillation, more preferably a low temperature distillation at a temperature around room temperature (below 40° C., preferably below 25° C.) and a reduced pressure (a pressure less than 100 hPa, preferably less than 10 hPa).

After distillative removal of the solvent, a clear liquid is present; after again adding solvent, preferably n-hexane, the main product cyclohexasiloxane $(H_2SiO)_6$ is obtained with a proportion of well above 90%. This observation demonstrates that the hexameric siloxane must be a relatively stable molecule. The smaller ring homologs rearrange to give it. This is a completely novel way of arriving in a controlled manner at a ring size of cyclosiloxanes of the $(H_2SiO)_6$ type.

When the solvent is removed briefly, the hexamer appears to form as a metastable intermediate. In the absence of solvent, it rearranges slowly to higher ring homologs. Preference is therefore given, after removing the solvent, to adding solvent again immediately or at least within 30 min, preferably within 5 min.

The readdition of solvent leads to quenching of the rearrangement process. When the solvent is removed for a longer period than 1 hour, impurities as a result of higher cyclosiloxane rings where n>6 disadvantageously form.

The cyclohexasiloxane $(H_2SiO)_6$ obtained, prepared selectively in this way, is storage-stable in solution.

The solvent used for the rearrangement to $(H_2SiO)_6$ is preferably an aprotic apolar solvent, more preferably n-hexane, n-pentane, cyclohexane or toluene.

For the rearrangement, after the removal of the solvent, dissolution is effected preferably in from 0.25 ml to 1 ml, more preferably from 0.4 to 0.6 ml, per mmol of originally used halosilane.

The invention is illustrated in detail below by working examples. All reactions were carried out under protective gas with Schlenk technology.

Commercially available starting materials were used and they were dried by appropriate laboratory methods.

WORKING EXAMPLE 1

Preparation of Cyclosiloxanes of the $(H_2SiO)_n$ Type, n=4 to 6, in n-hexane with Zinc Carbonate

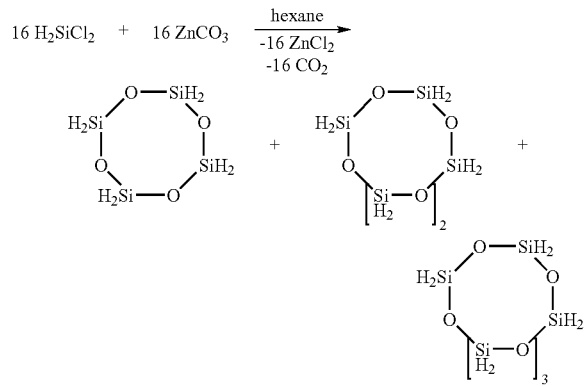

A Schlenk vessel (100 ml) with a magnetic stirrer bar is initially charged with 2.51 g (20 mmol) of zinc carbonate in 40 ml of n-hexane with ice cooling. Through a septum, with a syringe, 4.23 ml (20 mmol of dichlorosilane) of a 40% mixture of n-hexane and dichlorosilane are added. After the evolution of gas has ended, the solid (mainly $ZnCl_2$ and excess $ZnCO_3$) is filtered off from the solution through a Schlenk frit, and the solution is studied by NMR spectroscopy (nuclear magnetic resonance—DPX 400 Avance from Bruker, Rheinstetten, Germany by the DEPT 135 method) and by means of GC-MS (HP 5890 series II coupled to a mass-selective HP 5971 detector, use of a polymethylpolysiloxane column (30 m * 0.25 mm * 0.25 μm), injector and detector temperature 180° C.). The solid is washed repeatedly with n-hexane and dried in order to remove any adhering siloxane residues.

$^{29}$Si NMR Spectrum:
$\delta(H_2SiO)_4$=−46.6 ppm, $\delta(H_2SiO)_5$=−48.4 ppm,
$\delta(H_2SiO)_6$=−48.7 ppm,
ratio of tetramer $(H_2SiO)_4$: pentamer $(H_2SiO)_5$:
hexamer $(H_2SiO)_6$:
17.5% :14.0% :68.5%

$^1$H NMR Spectrum:
$\delta(H_2SiO)_4$=approx. 4.9 ppm, $\delta(H_2SiO)_5$=approx. 4.8 ppm, $\delta(H_2SiO)_6$=approx. 4.7 ppm GC-MS Characterization:
183 m/z $(H_2SiO)_4$; 229 m/z $(H_2SiO)_5$; 275 m/z $(H_2SiO)_6$ at a retention time of t=10.575 min.

The analysis results show that the synthesized product comprises the desired cyclosiloxanes of the $(H_2SiO)_n$ type, n=4-6, in very high purity (at least 98%).

WORKING EXAMPLE 2

Preparation of Cyclosiloxanes of the $(H_2SiO)_n$ Type in Toluene with Zinc Carbonate A Schlenk vessel (100 ml) with a magnetic stirrer bar is initially charged with 2.51 g (20 mmol) of zinc carbonate in 40 ml of toluene with ice cooling. Through a septum, with a syringe, 4.23 ml (20 mmol of dichlorosilane) of a 40% mixture of toluene and dichlorosilane are added. After the evolution of gas has ended, the solid is filtered off from the solution through a Schlenk frit and the solution is studied by NMR spectroscopy as described in working example 1.

$^{29}$Si NMR Spectrum:
$\delta(H_2SiO)_4$=−47.0 ppm, $\delta(H_2SiO)_5$=−48.6 ppm,
$\delta(H_2SiO)_6$=−48.8 ppm,
higher homologs at $\delta$=−48.9 ppm, $\delta$=−49.0 ppm and $\delta$=−50.0 ppm;

The analysis results show that the synthesized product comprises the desired cyclosiloxanes of the $(H_2SiO)_n$ type, n=4-6 (~95%); minor impurities (4-5%) of higher ring homologs are detectable.

WORKING EXAMPLE 3

Preparation of Cyclosiloxanes of the $(H_2SiO)_n$ Type in ethyl Acetate with Calcium Carbonate A Schlenk vessel (100 ml) with a magnetic stirrer bar is initially charged with 2.0 g (20 mmol) of calcium carbonate in 40 ml of ethyl acetate with ice cooling. Through a septum, with a syringe, 4.23 ml (20 mmol of dichlorosilane) of a 40% mixture of ethyl acetate and dichlorosilane are added. After the evolution of gas has ended, the solid is filtered off from the solution through a Schlenk frit and the solution is studied by NMR spectroscopy as described in working example 1.

$^{29}$Si NMR Spectrum:
$\delta(H_2SiO)_4$=−46.6 ppm, $\delta(H_2SiO)_5$=−47.9 ppm,
$\delta(H_2SiO)_6$=−48.3 ppm,
higher homologs at $\delta$=−48.4 ppm, $\delta$=−48.5 ppm and $\delta$=−49.5 ppm;
ratio of tetramer $(H_2SiO)_4$: pentamer $(H_2SiO)_5$:
hexamer $(H_2SiO)_6$:
20.4%:24.0%:55.6%

The analysis results show that the synthesized product comprises the desired cyclosiloxanes of the $(H_2SiO)_n$ type, n=4-6 (about 85%), but they are contaminated with higher ring homologs (about 15%).

WORKING EXAMPLE 4

Preparation of Cyclosiloxanes of the $(H_2SiO)_n$ Type in ethyl Acetate with Lithium Carbonate A Schlenk vessel (100 ml) with a magnetic stirrer bar is initially charged with 1.48 g (20 mmol) of lithium carbonate in 40 ml of ethyl acetate with ice cooling. Through a septum, with a syringe, 4.23 ml (20 mmol of dichlorosilane) of a 40% mixture of ethyl acetate and dichlorosilane are added. After the evolution of gas has ended, the solid is filtered off from the solution through a Schlenk frit.

$^{29}$Si NMR Spectrum:
$\delta(H_2SiO)_4$=−46.6 ppm, $\delta(H_2SiO)_5$=−48.0 ppm,
$\delta(H_2SiO)_6$=−48.3 ppm,
higher homologs at $\delta$=−48.5 ppm, $\delta$=−49.5 ppm and $\delta$=−49.7 ppm;
ratio of tetramer $(H_2SiO)_4$: pentamer $(H_2SiO)_5$:
hexamer $(H_2SiO)_6$:
24.7%:53.4%:21.9%

The analysis results show that the synthesized product comprises the desired cyclosiloxanes (about 85%), but they are contaminated with higher ring homologs (about 15%).

WORKING EXAMPLE 5

Preparation of (H$_2$SiO)$_6$ in n-hexane with Zinc Carbonate

A Schlenk vessel (100 ml) with a magnetic stirrer bar is initially charged with 2.51 g (20 mmol) of zinc carbonate in 40 ml of n-hexane with ice cooling. Through a septum, with a syringe, 4.23 ml (20 mmol of dichlorosilane) of a 40% mixture of n-hexane and dichlorosilane are added. After the evolution of gas has ended, the solid is filtered off from the solution through a Schlenk frit, and the solvent is removed by means of a low temperature distillation (generation of vacuum with liquid nitrogen, room temperature and pressure less than 100 hPa). After 5 min, new n-hexane was added, followed by characterization by means of NMR spectroscopy, as described in working example 1 (yield 57.6%).

$^{29}$Si NMR Spectrum:
δ(H$_2$SiO)$_6$=−48.8 ppm $^1$H NMR Spectrum:
δ(H$_2$SiO)$_6$=approx. 4.7 ppm The NMR data show that the desired compound (H$_2$SiO)$_6$ is present in a purity of greater than 95%.

The invention claimed is:

1. A process for preparing cyclosiloxanes of the type

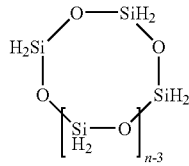

where n is equal to or greater than 3, comprising:
reacting
a.) a halosilane of formula H$_2$SiX$_2$ where X=halogen with
b.) at least one metal salt selected from the group consisting of a lithium salt, a copper(II) salt, a salt of a main group 2 metal, and a salt of a transition group 2 metal of the periodic table of the elements.

2. The process as claimed in claim 1, wherein the anion of the metal salt is carbonate or hydrogencarbonate.

3. The process as claimed in claim 1, wherein the metal salt is selected from the group consisting of zinc carbonate, calcium carbonate, lithium carbonate, copper carbonate, and magnesium carbonate.

4. The process as claimed in claim 1, wherein the halosilane is dichlorosilane.

5. The process as claimed in claim 1, wherein the reacting is performed at a temperature of from −80 to 40°C.

6. The process according to claim 1, wherein the reacting is carried out in an aprotic solvent.

7. The process as claimed in claim 6, wherein the aprotic solvent is selected from the group consisting of n-hexane, n-pentane, ethyl acetate, tetrahydrofuran, dioxane, toluene, cyclohexane, glyme and mixtures of these solvents.

8. The process as claimed in claim 6, wherein the reacting forms a product having the formula:

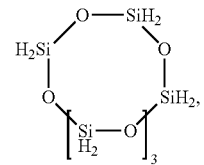

and, after the reacting, the product is concentrated by at least partly removing the solvent and then diluting by again adding the solvent.

9. The process as claimed in claim 8, wherein the removal of the solvent is carried out by distillation at a temperature below 40°C. and a pressure less than 100 hPa.

10. The process as claimed in claim 8, wherein the solvent is added again within 30 min after removal of the solvent.

* * * * *